United States Patent [19] [11] Patent Number: 4,691,063
Engel et al. [45] Date of Patent: Sep. 1, 1987

[54] ISOMERIZATION OF CRESOLS

[75] Inventors: Dusan J. Engel, Des Plaines, Ill.;
Jean-Pierre Gilson, Columbia, Md.

[73] Assignee: UOP Inc., Des Plaines, Ill.

[21] Appl. No.: 874,780

[22] Filed: Jun. 16, 1986

[51] Int. Cl.$^4$ .................. C07C 37/48; C07C 39/06
[52] U.S. Cl. ................................. 568/783; 502/77
[58] Field of Search ............... 568/783, 716; 502/77; 423/328

[56] References Cited

U.S. PATENT DOCUMENTS 3,702,886 11/1972 Argauer et al. .................. 423/328
3,965,208  6/1976 Butter et al. .................... 585/454
4,283,571  8/1981 Keim et al. ...................... 568/783
4,503,269  3/1985 Engel et al. ..................... 568/783
4,581,214  4/1986 Young ........................... 502/77 X Primary Examiner—Werren B. Lone
Attorney, Agent, or Firm—Thomas K. McBride; John F. Spears, Jr.; E. Jerome Maas

[57] ABSTRACT

An improvement in a process for the isomerization of cresols may be obtained by effecting the isomerization reaction of a cresol in the presence of a phosphorous containing crystalline aluminosilicate zeolite catalyst. The added phosphorous provides stability and longer life to the catalyst as well as more stable selectivity to the desired isomers. The isomerization reaction is effected at temperatures ranging from about 350° C. to about 500° C., pressures ranging from about 1 to about 60 atmospheres, a Liquid Hourly Space Velocity that ranges from 1 to about 5 hours$^{-1}$, with the abovementioned catalyst containing from about 1% to about 8% by weight phosphorous.

8 Claims, No Drawings

ISOMERIZATION OF CRESOLS

BACKGROUND OF THE INVENTION

Cresols may be prepared by the catalytic methylation of phenol. During the preparation, the predominant isomer which is obtained comprises o-cresol. While this particular isomer finds a wide variety of uses such as a disinfectant, as an organic intermediate or in the preparation of coumarine, the other isomers such as m-cresol and p-cresol are also important articles of commerce in the chemical industry. For example, m-cresol, in addition to being utilized as a disinfectant, will also find a use in fumigating compositions, in the production of synthetic resins, as a photographic developer, in nitrocresol explosives, as a use in ink, paint and varnish removers or in reclaiming rubber. Additionally, p-cresol is also used as a disinfectant, in fumigating composition, in dyestuffs and as an organic intermediate, etc. It is therefore incumbent to isomerize the predominantly o-cresol to the m- and p- isomers.

One such method for the isomerization of o-cresol is found in U.S. Pat. No. 4,283,571. This patent teaches the catalytic isomerization of o-cresol by utilizing an acid-acting crystalline aluminosilicate zeolite of the ZSM type. The patent describes that the crystal structure of the zeolite should possess a pore dimension greater than about 5 Angstroms and a constraint index of from about 1.0 to about 12.0. The crystalline aluminosilicate zeolites will possess a definite crystalline structure in which are positioned a relatively large number of small cavities which are interconnected by a number of still smaller channels. The zeolites are known to possess catalytic properties, especially concerning those processes found in the petroleum refining field. These processes include cracking, hydrocracking, isomerization of n-paraffins and naphthenes, polymerization of compounds containing an olefinic or acetylenic linkage, reforming, alkylation, etc. The zeolite materials which are preferred for many of these processes possess a constraint index within the range hereinbefore set forth as well as containing a silica to alumina mole ratio between about 10 and about 85. An example of a crystalline aluminosilicate zeolite which may be used comprises that type which is set forth in U.S. Pat. No. 3,702,886.

Another method for the isomerization of cresols is found in U.S. Pat. No. 4,503,269. This patent teaches the catalytic isomerization of cresols by utilizing an acidic acting crystalline aluminosilicate zeolite of the ZSM type in the presence of added hydrogen, thereby affording an increase in isomerization to the para-isomer as well as a total increase of cresols and an improved product color.

The process of isomerizing cresols utilizing an aluminosilicate zeolite is known, but we have discovered that by effecting the isomerization reaction in the presence of a phosphorous containing crystalline aluminosilicate zeolite, it is possible to obtain beneficial and unexpected results, these results being shown further in greater detail.

BRIEF SUMMARY OF THE INVENTION

This invention relates to a process for the isomerization of cresols. More specifically, the invention is concerned with an improvement in the isomerization of cresols utilizing a phosphorous-containing crystalline aluminosilicate zeolite material as the catalyst for the reaction.

As explained before, the isomeric cresols are useful articles and the isomerization of the predominant o-cresol fraction to the m and p isomers has been effected by utilizing a zeolitic material as the catalyst for the reaction. However, we have now discovered that by effecting the isomerization reaction in the presence of a phosphorous-containing acidic crystalline aluminosilicate zeolitic substance, several beneficial results are obtained. As explained further in the examples, both an increase in the life of the catalyst and an improvement in the selectivity to the para-cresol isomer are effected using the above-mentioned catalyst.

It is therefore an object of this invention to provide a process for the isomerization of cresols in which there is found an increased selectivity to the para-isomer.

A further object of this invention is to provide a more stable and therefore longer lived aluminosilicate zeolitic catalyst for use in the isomerization of cresols.

In one aspect an embodiment of this reaction is found in a process for the isomerization of a cresol which comprises treating said cresol in the presence of an acidic crystalline zeolite catalyst containing phosphorous at isomerization conditions and recovering the resultant isomers.

A specific embodiment of this invention is found in a process for the isomerization of o-cresol which comprises treating said cresol at a temperature in a range of from about 400° C. to about 460° C., a pressure in a range of from about 1 to about 5 atmospheres, a Liquid Hourly Space Velocity city of from about 1 to about 3 hours$^{-1}$, in the presence of a phosphorous containing acid-acting crystalline aluminosilicate catalyst in which the phosphorous is present at 2.5% by weight, and recovering the resultant isomerized product comprising m-cresol and p-cresol.

Other objects and embodiments will be found in the following further detailed description of the invention.

DETAILED DESCRIPTION OF THE INVENTION

As hereinbefore set forth, the present invention is concerned with an improvement in a process for the isomerization of a cresol whereby certain advantages previously mentioned may be attained. The extension of the stability and lifetime of the catalyst which is employed in the reaction will have a beneficial result in the overall cost of the process, thereby contributing to the commercial attractiveness of this process. The isomerization process is effected by treating a cresol such as o-cresol or m-cresol at treatment conditions in the presence of a phosphorous containing acidic crystalline aluminosilicate zeolite.

As was previously mentioned, the crystalline aluminosilicate zeolite which is employed as the catalyst for the present process possesses a constraint index of from about 1 to about 12 and also possesses a silica-to-alumina ratio of from about 10 to about 100, such as from to about 10 about 85. An exemplary acidic crystalline aluminosilicate zeolite comprises an acidic ZSM-5 type zeolite. The treatment conditions which are employed to effect the isomerization will include temperatures ranging from about 350° C. to about 500° C. and preferably in the range of from about 400° C. to about 460° C.; a pressure in the range of about 1 to about 60 atmospheres, and preferably in the range of about 1 to about 5 atmospheres; and a Liquid Hourly Space Velocity in a range of from about 1 to about 5 hours$^{-1}$, and preferably from about 1 to about 3 hours$^{-1}$. The pressures which are employed at treatment conditions are due to the addition of hydrogen which is charged to the reactor in an amount so that the hydrogen present will be in a molar ratio of from about 1:1 to about 10:1 and preferably from about 2 to about 6 moles of hydrogen to moles of cresol. Alternatively, the operating pressures which are employed may be attained by a partial pressure of hydrogen, the remainder being due to the addition of inert gasses such as nitrogen, helium, argon, etc., into the reaction vessel.

The phosphorous containing acidic crystalline aluminosilicate zeolite can have a range of from about 1% to about 8% phosphorous by weight with a preferable range from about 2% to about 5%, and is prepared by mixing an aqueous solution of ammonium hydrogen phosphate at 70° C. with the acidic form of the zeolite. After a very slow stirring for several hours at 90°, the liquid is decanted from the solid which is then dried and calcined to form the phosphorous modified acidic zeolite catalyst.

Phosphorous modification of a crystalline aluminosilicate catalyst manifests itself in a change of the active acidic sites of the catalyst apparently by attachment to a silicon hydroxy group and/or an aluminum hydroxy group as suggested in the literature. Analysis of the acid sites was performed using Temperature Programmed Desorption (TPD) of ammonia from the catalyst wherein the ammonia bound to the strongest active sites will be released at the highest temperature. TPD analysis cannot give a precise number of active sites but can show relative numbers of the weak, medium, and strong active sites, and, based on this analysis, it was apparent that the phosphorous modification reduced the numbers of strong and medium sites in the present catalyst in comparison to the non-phosphorous modified catalyst.

The isomerization of the o-cresol or m-cresol may be effected in any manner, either by a batch type operation or a continuous type operation. For example, when a batch type operation is employed, a quantity of the cresol along with the catalyst is placed in an appropriate apparatus such as an autoclave of the rotating, mixing or stirring type. The cresol and the catalyst will generally be present in a weight ratio of cresol to catalyst of from about 3:1 to about 100:1. The autoclave is sealed and hydrogen is pressed in until the desired initial operating pressure has been reached. Following this, the autoclave and contents thereof are heated to the desired operating temperature and maintained thereat for a predetermined period of time which may range from about 0.5 up to about 10 hours or more in duration. At the end of this time, heating is discontinued and after the autoclave and contents thereof have returned to room temperature, the excess pressure is discharged, the autoclave is opened, and the reaction mixture is recovered therefrom. After separation from the catalyst, the reaction products are subjected to conventional means of separation which may include fractional distillation or selective adsorption/desorption whereby the desired isomers of o-cresol, m-cresol and p-cresol are separated and recovered.

Alternatively, the isomerization reaction may be effected in a continuous manner of operation. When this type of operation is utilized, a quantity of the catalyst is placed in an appropriate apparatus which is maintained at the proper operating conditions of temperature and pressure. Following this, the o-cresol or m-cresol which is to be isomerized is continuously charged to this reactor along with the hydrogen. After passage through the reactor for a predetermined period of time, the reactor effluent is continuously withdrawn and subjected to conventional means of separation whereby the desired isomers are separated and recovered, the unreacted o-cresol or m-cresol being recycled to the reactor to form a portion of the feedstock thereto.

Inasmuch as the catalyst is in solid form, various types of continuous reactions may be employed. For example, the catalyst may be maintained in the reactor as a fixed bed and the feedstock passed over the catalyst bed in either an upward or downward flow. Another type of continuous operation which may be effected comprises a moving bed type in which the catalyst and the feedstock are passed through the reactor either concurrently or countercurrently to each other. Alternatively, if so desired, the catalyst may be carried into the reactor as a slurry in the feedstock.

As can be seen from the following examples, it is preferred to operate this invention in a continuous mode at vapor phase conditions, thereby providing isomerization of o-cresol to the preferred p-cresol in the greatest selectivity.

The following examples are given for purposes of illustrating the results which are obtained when utilizing the improvements set forth in the present specification and appended claims. However, it is to be understood that these examples are merely illustrative in nature and that the present invention is not necessarily limited thereto.

EXAMPLE I

The acidic zeolitic isomerization catalyst used in this invention for comparison purposes was prepared by placing 500 g of a sodium ZSM-5 type catalyst in a 5 liter flask and stirred with 1,000 ml of 13% nitric acid for 30 minutes. After stirring, the contents of the flask were filtered through coarse filter paper and then the filter cake was placed back in the original flask to be stirred with 1,000 ml of deionized water for 10-15 minutes. The contents of the flask was filtered as before and washed until the pH was neutral. The solid was dried overnight at 105° C. and calcined first at 350° C. for one hour followed by calcination at 550° C. for four hours. The acidic zeolite (HZ) was then mixed with a low colloidal silica as a binder and extruded as an 80% HZ—20% silica extrudate which was dried and calcined as before.

Alternatively, the catalyst was prepared by placing 250 g of the sodium zeolite material in a 5 liter flask and stirring it with 2,300 ml of 5% ammonium nitrate solution at 80°-85° C. for about 20 minutes. After cooling to 50° C., the contents of the flask were filtered, the filter cake was stirred with a new 2,300 ml portion of 5% ammonium nitrate solution, and this procedure repeated three times. The resultant solid was then washed four times by slurrying in a liter of water with stirring for 10-15 minutes. The final wash on the filter used 1.5 liters of water. The filter cake was dried at 105° C. for 12 hours, calcined at 350° C. for one hour, and calcined at 550° C. for 3 hours.

EXAMPLE II

The phosphate modified acidic zeolite catalyst (PHZ) used in this invention was formed by dissolving 10 g of ammonium monohydrogen phosphate in 38 ml of water, heating to 70° C., adding 20 g of the acidic zeolite as formed by either preparation of Example I, and maintaining this stirred mixture at 90° C. for 2 hours. After decantation, the solid was dried at 90°–105° C. for 2 hours and calcined at 500° C. for 2 hours.

EXAMPLE III

The isomerization of o-cresol was effected by placing 20 cc (10.3 grams) of the catalyst prepared as in Example I above in a reactor having a ½" inner diameter. Following this, o-cresol was charged up-flow to the reactor at a Liquid Hourly Space Velocity (LHSV) of 1.0 hours$^{-1}$ while maintaining a pressure of 60 atmospheres at a temperature of 380° C. and with a hydrogen-to-o-cresol feed ratio of 2:1, thereby maintaining a liquid phase reaction. After a period of 20 hours, the LHSV was increased to 3.0 hours$^{-1}$ for an additional 24 hours. The reactor effluent was subjected to gas chromatographic analysis with the results used to calculate the conversion rates and selectivities shown in Table I below.

TABLE I

ISOMERIZATION OF O-CRESOL

| Stream Hours | o-Cresol % Conversion | Selectivities % | | | |
|---|---|---|---|---|---|
| | | m- | p- | m & p | Heavies |
| 4 | 54.4 | 66.7 | 21.3 | 88.0 | 2.7 |
| 8 | 56.4 | 69.5 | 22.7 | 92.2 | 2.1 |
| 12 | 54.2 | 71.8 | 23.6 | 95.4 | 0.9 |
| 16 | 52.0 | 71.2 | 23.7 | 94.9 | 1.2 |
| 20 | 51.9 | 70.9 | 23.1 | 94.0 | 1.1 |
| 24 | 41.3 | 74.1 | 23.5 | 97.6 | 0.5 |
| 28 | 33.3 | 75.7 | 23.7 | 99.4 | 0.1 |
| 32 | 31.8 | 75.5 | 23.9 | 99.4 | 0.1 |
| 36 | 31.4 | 75.5 | 23.4 | 99.4 | 0.1 |

EXAMPLE IV

The isomerization of o-cresol was effected as in ample III using the catalyst of the present invention as made in Example II. The results of analyses of the product obtained in this run are set forth in Table II below:

TABLE II

ISOMERIZATION OF O-CRESOL

| Stream Hours | o-Cresol % Conversion | Selectivities % | | | |
|---|---|---|---|---|---|
| | | m- | p- | m & p | Heavies |
| 4 | 20.9 | 66.0 | 24.9 | 90.9 | 0 |
| 8 | 16.7 | 71.3 | 28.7 | 100 | 0 |
| 16 | 13.5 | 70.4 | 29.6 | 100 | 0 |
| 20 | 12.0 | 69.2 | 30.8 | 100 | 0 |
| 28 | 4.6 | 71.7 | 28.3 | 100 | 0 |
| 32 | 4.0 | 72.5 | 27.5 | 100 | 0 |
| 36 | 3.4 | 70.6 | 29.4 | 100 | 0 |

A comparison of the data from Tables I and II will show that the selectivity toward p-cresol is enhanced from 3 to 5% through the use of the phosphorous containing catalyst.

EXAMPLE V

The isomerization of o-cresol was effected as in Example III utilizing the catalyst of Example I but at downflow vapor phase conditions wherein the pressure was 5 atmospheres, the Liquid Hourly Space Velocity (LHSV) was held constant at 1.0 hours$^{-1}$, and the hydrogen to feed ratio was at 6:1 for the first 24 hours and at 2:1 for an additional 24 hours. The gas chromatographic data was reduced as before and is shown in Table III below.

TABLE III

ISOMERIZATION OF O-CRESOL

| Stream Hours | Hydrogen O-Cresol | o-Cresol % Conversion | Selectivities % | | | |
|---|---|---|---|---|---|---|
| | | | m- | p- | m & p | Heavies |
| 4 | 6:1 | 15.8 | 65.8 | 24.7 | 90.5 | 0.7 |
| 8 | 6:1 | 13.5 | 71.1 | 27.4 | 98.5 | 0.1 |
| 12 | 6:1 | 11.2 | 71.4 | 28.6 | 100 | 0 |
| 16 | 6:1 | 10.4 | 72.1 | 27.9 | 100 | 0 |
| 24 | 6:1 | 9.5 | 71.6 | 28.4 | 100 | 0 |
| 32 | 2:1 | 11.8 | 71.3 | 27.0 | 98.3 | 0 |
| 40 | 2:1 | 11.8 | 74.6 | 24.6 | 99.2 | 0 |
| 48 | 2:1 | 10.3 | 74.8 | 25.2 | 100 | 0 |

As can be seen from Table III, in order to have a high selectivity of p-cresol, a larger amount of hydrogen must be present but the conversion of o-cresol is very low in the vapor phase using the acidic catalyst.

EXAMPLE VI

The isomerization of o-cresol was effected by placing 20 cc (10.3 grams) of the catalyst of the present invention prepared according to Example II in a reactor having a ½" inner diameter. Following this, o-cresol was charged upflow to the reactor at a Liquid Hourly Space Velocity (LHSV) of 1.0 hours$^{-1}$ while maintaining a pressure of 60 atmospheres and a temperature of 460° C. After a period of 16 hours, the LHSV was increased to 3 hours$^{-1}$ for an additional 16 hours. The hydrogen-to-o-cresol feed ratio was maintained at 2:1 throughout the entire liquid phase reaction period. The reactor effluent was subjected to gas chromatographic analysis with the results used to calculate the conversion rates and selectivities shown in Table IV below.

TABLE IV

ISOMERIZATION OF O-CRESOL

| Stream Hours | LHSV Hours$^{-1}$ | o-Cresol % Conversion | Selectivities % | | | |
|---|---|---|---|---|---|---|
| | | | m- | p- | m & p | Heavies |
| 4 | 1 | 41.2 | 70.4 | 23.5 | 93.9 | 2.7 |
| 8 | 1 | 40.4 | 70.8 | 23.3 | 94.1 | 2.5 |
| 12 | 1 | 40.7 | 70.3 | 23.1 | 93.4 | 2.5 |
| 16 | 1 | 40.5 | 71.6 | 23.5 | 95.1 | 2.5 |
| 20 | 3 | 30.8 | 73.1 | 23.1 | 96.2 | 1.3 |
| 24 | 3 | 24.5 | 75.5 | 21.2 | 96.7 | 1.6 |
| 28 | 3 | 24.5 | 74.3 | 22.4 | 96.7 | 2.8 |
| 32 | 3 | 25.3 | 77.1 | 20.0 | 97.1 | 2.0 |

EXAMPLE VII

The isomerization of o-cresol was effected by placing 22 cc (10.3 grams) of the catalyst of the present invention prepared according to Example II in a reactor having a ½" inner diameter. Following this, o-cresol was charged downflow to a reactor at a Liquid Hourly Space Velocity (LHSV) of 1.0 hours while maintaining a temperature of 460° C., a pressure of 5 atmospheres and a hydrogen-to-o-cresol ratio of 6:1. After a period of 20 hours, the hydrogen to o-cresol ratio was decreased to 2:1 for an additional 24 hours. The reactor effluent was subjected to gas chromatographic analysis and the results used to calculate the conversion rates and selectivities shown in Table V below:

TABLE V

ISOMERIZATION OF O-CRESOL

| Stream Hours | LHSV Hours$^{-1}$ | o-Cresol % Conversion | Selectivities % | | | |
|---|---|---|---|---|---|---|
| | | | m- | p- | m & p | Heavies |
| 4 | 1 | 35.6 | 69.4 | 27.8 | 97.2 | 0.8 |

TABLE V-continued
ISOMERIZATION OF O-CRESOL

| Stream Hours | LHSV Hours⁻¹ | o-Cresol % Conversion | Selectivities % m- | p- | m & p | Heavies |
|---|---|---|---|---|---|---|
| 8 | 1 | 30.3 | 69.6 | 29.4 | 99.0 | 0 |
| 12 | 1 | 26.6 | 68.8 | 30.1 | 98.9 | 0 |
| 16 | 1 | 24.0 | 69.2 | 30.8 | 100.0 | 0 |
| 20 | 1 | 22.7 | 68.3 | 31.3 | 99.6 | 0 |
| 28 | 1 | 24.4 | 70.1 | 29.5 | 99.6 | 0 |
| 32 | 1 | 23.8 | 70.6 | 29.0 | 99.6 | 0 |
| 36 | 1 | 23.6 | 70.3 | 28.8 | 99.1 | 0 |
| 40 | 1 | 23.1 | 71.0 | 29.0 | 100.0 | 0 |
| 44 | 1 | 22.8 | 70.6 | 28.6 | 99.2 | 0 |

A comparison of the results set forth in Table IV and Table V clearly illustrates that the preferred mode of operation is a vapor phase, down-flow isomerization reaction giving an average para-cresol selectivity of 29.4% versus a 22.5% selectivity when using an up-flow, liquid phase operation.

EXAMPLE VIII

After a thorough washing with acetone and drying, carbon and hydrogen analyses were performed on the used catalysts of Examples III to VII. The used catalyst that was only an acidic crystalline aluminosilicate zeolite (HZ) was black in color while the catalyst that had been phosphorous modified (PHZ) as in Example II was beige in color. The results are shown in Table VI wherein the Liquid Hourly Space Velocity is represented by LHSV and the feed consisted of ortho cresol.

TABLE VI
CARBON-HYDROGEN ANALYSES OF USED CATALYST

| Operation Phase | Hrs On Stream | LHSV | Temperature °C. | Catalyst | % Carbon | % Hydrogen |
|---|---|---|---|---|---|---|
| Liquid | 40 | 1,3 | 380 | HZ | 9.04 | 0.84 |
| Liquid | 44 | 1,3 | 380 | HZ | 8.01 | 0.81 |
| Liquid | 36 | 1,3 | 380 | PHZ | 4.59 | 0.73 |
| Vapor | 44 | 1 | 460 | PHZ | 4.16 | 0.84 |

As can be seen from the above table, coking of the catalyst was less severe in the phosphorous containing catalyst (PHZ), thereby indicating a longer life and greater stability for this catalyst.

We claim as our invention:

1. A process for the isomerization of a cresol selected from the group consisting of o-cresol and m-cresol which comprises contacting said cresol in the vapor phase with an acidic phosphorous-containing crystalline zeolite catalyst at isomerization conditions and recovering the resultant isomers.

2. The process as set forth in claim 1 in which said isomerization conditions include a temperature in the range of from about 350° C. to about 500° C., a pressure in the range of from about 1 to about 60 atmospheres and a Liquid Hourly Space Velocity in a range of from 1 to about 5 hours⁻¹.

3. The process as set forth in claim 1 in which said acidic crystalline zeolite comprises an aluminosilicate possessing a silica-to-alumina ratio in the range of from about 10 to about 100.

4. The process as set forth in claim 3 in which said acidic crystalline zeolite is an acidic ZSM-5 zeolite.

5. The process as set forth in claim 4 in which said acidic crystalline zeolite contains from about 1% to about 8% by weight of phosphorous.

6. The process as set forth in claim 1 in which said cresol is present in a weight ratio to catalyst in the range of from about 3:1 to about 100:1.

7. The process as set forth in claim 1 in which said cresol is o-cresol and said isomers comprise m-cresol and p-cresol.

8. The process as set forth in claim 1 in which said cresol is m-cresol and said isomers comprise p-cresol and minor amounts of o-cresol.

* * * * *